United States Patent [19]
Yoon et al.

[11] Patent Number: 5,834,771
[45] Date of Patent: Nov. 10, 1998

[54] ION MOBILITY SPECTROMETER UTILIZING FLEXIBLE PRINTED CIRCUIT BOARD AND METHOD FOR MANUFACTURING THEREOF

[75] Inventors: Kyoung Won Yoon; Ki Woon Hwang; Ho Jin Lim; Seung Ki Choi; Hark Sang Kim, all of Daejon, Rep. of Korea

[73] Assignee: Agency for Defence Development, Daejon, Rep. of Korea

[21] Appl. No.: 838,211

[22] Filed: Apr. 16, 1997

Related U.S. Application Data

[63] Continuation of Ser. No. 352,333, Dec. 8, 1994, abandoned.

[30] Foreign Application Priority Data

Jul. 8, 1994 [KR] Rep. of Korea ................. 1994/16498

[51] Int. Cl.$^6$ ............................. B01D 59/44; H01J 49/00
[52] U.S. Cl. ........................................... 250/286; 250/287
[58] Field of Search ................................... 250/281, 286, 250/287

[56] References Cited

U.S. PATENT DOCUMENTS

| | | |
|---|---|---|
| 4,390,784 | 6/1983 | Browning et al. . |
| 4,551,624 | 11/1985 | Spangler et al. . |
| 4,712,008 | 12/1987 | Vora et al. . |
| 4,777,363 | 10/1988 | Eiceman et al. . |
| 4,923,932 | 5/1990 | Katayose et al. ................. 525/391 |
| 5,053,343 | 10/1991 | Vora et al. . |
| 5,109,157 | 4/1992 | Loen . |
| 5,112,462 | 5/1992 | Swisher ................................ 205/165 |
| 5,200,614 | 4/1993 | Jenkins . |

*Primary Examiner*—Bruce Anderson
*Attorney, Agent, or Firm*—Townsend and Townsend and Crew LLP

[57] ABSTRACT

There is an ion mobility spectrometer(IMS) comprising a ion drift tube comprising a reaction region, a shutter grid, a drift region and a collector; an inlet for introducing a carrier gas into the reaction region; and an ionization source in the reaction region, wherein flexible PCBs (printed circuit board) are fixed onto the surface of the ion drift tube to develop electric fields along the axis of the reaction region and the drift region for the movement of ions generated in the reaction region to the collector.

8 Claims, 2 Drawing Sheets

ION MOBILITY SPECTROMETER UTILIZING FLEXIBLE PRINTED CIRCUIT BOARD AND METHOD FOR MANUFACTURING THEREOF

This is a Continuation of application Ser. No. 08/352,333, filed Dec. 8, 1994 now abandoned, the disclosure of which is incorporated by reference.

BACKGROUND OF THE INVENTION

1. Field of the Invention

The present invention relates to an ion mobility spectrometer(IMS) comprising a ion drift tube comprising a reaction region, a shutter grid, a drift region and a collector, wherein flexible printed circuit board (PCB) is fixed onto the surface of the ion drift tube to develop electric fields along the axis of the reaction region and the drift region for the movement of ions generated in the reaction region to the collector, which enables a manufacturing process to be simple and exhibits a superior analysis performance.

2. Description of the Prior Art

The ion mobility spectrometer(IMS) was developed in the early 1970's in order to detect and analyze organic vapors or contaminants in the atmosphere. A typical ion mobility spectrometer detector cell (ion drift tube) comprises a reaction region for generating ions and a drift region for separating ions and a collector. A shutter grid is positioned between the reaction region and drift region which controls the flow of ions to the drift region. A carrier gas together with a sample gas introduced into the ion mobility spectrometer through the inlet is ionized by radioactive materials such as, for example, Ni-63, Am-241, tritium, etc. in the reaction region. Coronas from multipoint or wire array, electrons produced by photoemission and multiphotoionization have also been proposed or used as methods to generate ions in the IMS.

The ions formed through these processes move to the collector under the influence of drift field which is applied along the ion drift tube. The mixture of ions separated into individual ions before arrival at the collector by the collision of drift gas which flows in the opposite direction of ion flow and each ion shows unique velocity due to their mass, size, and charge. The separated ions produce current by collision to the collector. Until the ion in the drift region arrive to the collector other ions in the reaction region are cut off from flowing into the drift region by the electric field applied to the shutter grid. Typically the shutter grid opens for 0.5–2 ms in the period of about 50 ms. A shutter grid consists of two arrays which have parallel wires electrically isolated from each other. If the same voltage is applied to each array, the mixture of ions generated in the reaction region flows into the drift region. And if an electric bias which generates an electric field stronger than 3 times the drift field is applied to the shutter grid, the mixture of ions in the drift region are cut off from going through the grid. The drift velocities and the peak current of the ions arriving at the collector provides a basis for the identification of the chemical species and amounts originally introduced into the reaction region.

The characteristics of the ion mobility spectrometer depend on the ion drift tubes used as detector cells which generate, separate and collect ions. The structures of ion drift tubes are different from each other according to the methods of applying electric fields to the reaction region and drift region. Ion drift tubes development since the first IMS may be classified into three designs, conductively inlaid tube design, stacked ring design, and ion lens design.

First, in U.S. Pat. No. 4,390,784, issued on Mar. 29, 1984 to D. R. Browning et al., an ion mobility spectrometer which utilized ceramic tubes with a resistive coating on their inner walls is described. If an electric voltage is applied to both ends of resistive composition of conductively inlaid tubes, then an electric field develops along the axis of the tubes. This is called an ion drift tube of CIT (Conductively Inlaid Tube) design. Second, in U.S. Pat. No. 4,777,363 issued on Oct. 11, 1988 to G. A. Eiceman and C. S. Leasure, an ion mobility spectrometer is described which utilized cylindrical tubes consisting of a series of stacked cylindrical metal rings spaced with insulators such as alumina or macor rings (sapphire balls may also be used).

Through proper resistor biasing the rings are placed at potentials relative to their position within the tube, so that a uniform electric field is developed along the axis of the tube. This is called an ion drift tube of stacked ring design. Third, the ion drift tube used in the Advanced Vapor Monitor and explosive detector PD-5 produced by Graseby Ionics Ltd. in the United Kingdom has a series of thin metal disks which are separated from each other by insulator rods at the fringes of the disks. Through proper resistor biasing the disks placed at potentials relative to their position within the tube, so that a uniform electric field is developed along the axis of the device. This is called an ion drift tube of ion lens design. Many ion drift tubes with similar designs to the ion drift tubes described above have been issued as patents.

The ion drift tubes described above have quite a few critical limitations, respectively. In the CIT design, a uniform electric field could be developed, and thus exhibits better performance than the IMS utilizing another design. But critical problems such as the technique of coating resistive composition onto the inner walls of the tube with constant thickness and difficulty in mass production are the disadvantages. Fabrication of an IMS of stacked ring or ion lens design, is not easy because they consists of many items such as metal rings, insulator rings, clamps and their performance is poor due to the non-linear electric field in the drift tubes. Thus there are many efforts to develop an ion drift tube of new design having better performance, easier process of fabrication and cheaper production cost.

SUMMARY OF THE INVENTION

The object of the present invention is to provide an ion mobility spectrometer, which comprises a ion drift tube comprising a reaction region, a shutter grid, a drift region and a collector, an inlet for introducing a carrier gas into the reaction region and an ionization source in the reaction region, wherein flexible PCBs (printed circuit board) are fixed onto the surface of the ion drift tube to develop electric fields along the axis of the reaction region and the drift region for the movement of ions generated in the reaction region to the collector.

The present invention utilizes a flexible PCB instead of conductive rings, conductive disks, and resistive coating as in the conventional IMS to develop electric fields along the axis of the ion drift tube, so an IMS made by using the present invention will be light and can be of various size. As it is easy to control the pattern of flexible PCB, uniform electric field may be developed like in the CIT design. Flexible PCB of various patterns can be made reproducibly in mass production and can be fixed easily onto the surface of the insulator cylinder.

The ion mobility spectrometer according to the present invention can be produced by an easy process of production, has high analyzing performance, no limit in size and light weight.

DETAILED DESCRIPTION OF THE INVENTION

The invention provides an ion mobility spectrometer for developing an electric field along the axis of an ion drift tube made of dielectric material by using a flexible PCB fixed onto the outer surface and/or the inner surface of the tube. Patterns on the flexible PCB may be parallel conductive bands separated from each other and the conductive bands are electrically connected to adjacent bands via resistors, chip resistors or resistive composition. The flexible PCB should be long enough to enclose the reaction region and the drift region. Through proper resistor biasing the conductive bands are placed at potentials relative to their positions of the tube, so that a uniform electric field is developed along the axis of the cylinder.

The insulator enclosing a reaction region and a drift region of a ion drift tube is surrounded with insulating materials with high dielectric constant, high temperature compatibility, and chemical resistance, for example, ceramics, boron nitride, alumina, glass, plastic, mica, FRP, etc.

Flexible PCB in the present invention may be of any commercial flexible PCBs available now or developed in the future. Bendable PCB may be used instead of flexible PCB in the invention as well.

Furthermore, in the present invention the flexible PCB may be fixed onto the surface of insulator cylinder enclosing the reaction region and the drift region.

Furthermore, in the present invention flexible PCB may be fixed onto the outer and/or inner surface of the conductive cylinder instead of the insulator cylinder.

In the present invention the flexible PCB may be fixed by adhesives with high temperature compatibility and chemical resistance, such as organic adhesive, silicon sealant, and ceramic adhesive or by a fixing device or material, such as, clamps, tape, and bands.

In the present invention a material having chemical resistance, for example, teflon or ceramics may be coated onto the surface of the flexible PCB.

Figure 1:
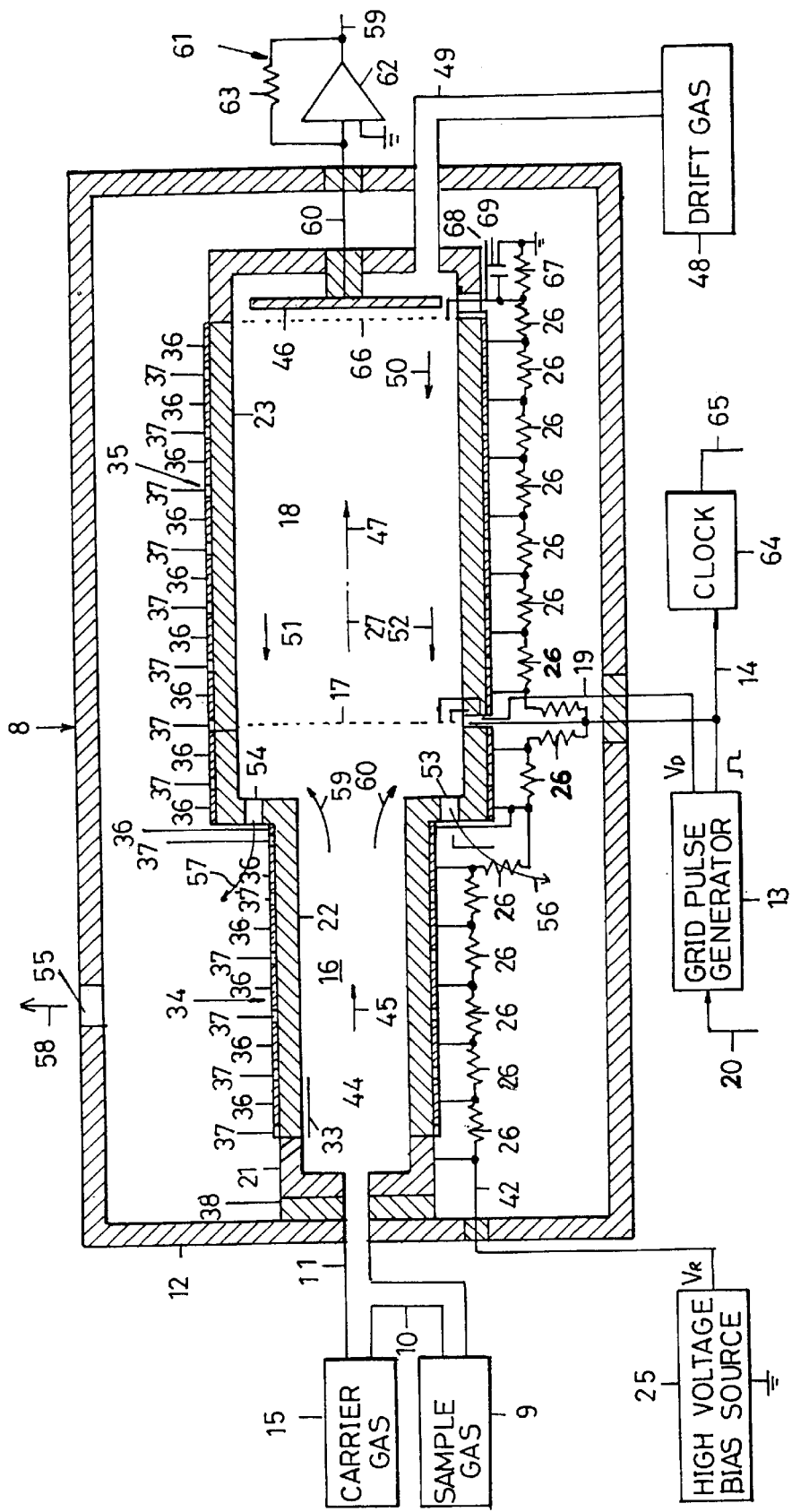
FIG. 1 is a cross-section at view showing an ion mobility spectrometer according to the present.

Other objects, features and advantages of the present invention will become more apparent to those skilled in the art from the following detailed description of the preferred embodiments and certain modifications therefore when taken together with the drawings. Referring to FIG. 1, an ion mobility spectrometer (IMS) 8 is shown for identifying one or more constituents in a sample gas 9. A carrier gas 15 with sample gas 9 passes through inlet port 11 of housing 12 into a reaction region 16. The carrier gas may be, for example, a high purity gas, such as nitrogen or purified air, as well as ambient air. Sample gas 9 may be injected into the carrier gas by means of, for example, an orifice 10 as shown in FIG. 1, a syringe, a membrane inlet, an injection port, as well as a gas chromatographic column in gas chromatography. A preconcentration device, or other suitable sample delivery means depending on various applications may be used.

Reaction region 16 and drift region 18 are surrounded by two dielectric cylinders with high temperature compatibility and chemical resistance, for example, Macor, ceramic, boron nitride, alumina, glass, plastic, mica, FRP with flexible PCBs 34, 35 onto the outer surface of them by silicon sealant. Macor is an industrial processed ceramic, as described in 1974 Technical Data Sheet AX-3000 from Duramic Products, Inc., Pallisades Park, N.Y., U.S.A. The pattern of flexible PCB 34 and 35 was photo-etched with a product from the Rogers Corporation, Chandler, Ariz., U.S.A. The patterned flexible PCBs 34 and 35 fixed onto the outer surface of reaction region cylinder 22 and drift region cylinder 23 have patterns of 5 parallel metal bands 36 and 9 parallel metal bands 36 respectively. The metal bands are apart from each other and connected to adjacent metal bands via resistors. Chip resistors, or resistive composition may be used instead of resistors. The performance of the IMS depends on the number and the width of the bands and the flexible PCB may be patterned optionally.

Reaction region 16 and drift region 18 may be heated to 250° C. by heating tapes or resistance wires wrapped around housing 12. A high voltage bias source 25 is connected across a voltage divider 42 comprising a plurality of resistors 26 coupled in series to progressively apply increasing voltages to the conductive bands 36, to create a voltage gradient in the reaction region 16 and drift region 18.

A shutter grid 17 divides the reaction region 16 from the drift region 18 and functions to cut off ions entering the drift region 18 until a pulse is received from a grid pulse generator 13 over lead 14. The shutter grid 17 may consist of a planar array of parallel wires with every other wire in electrical contact with each other and to lead 14.

Alternatively, the shutter grid may be a parallel plane shutter grid consisting of two grids displaced apart from each other along the axis 27 of the IMS cell 8. The other wires are coupled together and to lead 19 at voltage Vd. When the grid pulse generator 13 provides a first voltage different from voltage Vd to lead 14, ions generated in reaction region 16 are collected by the grid wires 17 and are not allowed to enter drift region 18. When the grid pulse generator 13 momentarily provides a second voltage Vd to lead 14, ions generated in the reaction region 16 are allowed to enter drift region 18 without being collected by grid wires 17. The grid pulse generator 13 is referenced to the voltage divider circuit 42 by means of lead 19 and is isolated from low voltage control circuitry, for example, by optoisolators. Grid pulse generator 13 may be free running or may receive a control signal over lead 20.

High energy radiation from the radioactive material Ni-63 33 in the reaction region ionize a carrier gas introduced through the inlet 11 into the reaction region 16 to generate negative and positive reactant ions. Radioactive materials such as Am-241, Tritium, etc, may be used instead of Ni-63. These reactant ions react with sample gas 9 to form positive and negative product ions. According to the polarity of high voltage bias source 25 only positive or negative ions can move along the axis of the arrow 45. At positive polarity only positive ions move along the axis of the arrow 45 and negative ions are collected to the surface of the cylinder 22 surrounding reaction region 16. On the other hand at negative polarity, only negative ions move along the axis of the arrow 45 and positive ions are collected to the surface of the cylinder 22 surrounding reaction region 16.

Periodically, shutter grid 17 is momentarily biased by a voltage pulse on lead 14 to enter ions 44 into the drift region 18. Within drift region 18, ions 44 move or accelerate towards collector 46 as shown by arrow 47. A stream of non-reactant drift gas 48 is injected into port 48 and passes through drift region 18, as shown by arrows 50, 52. Drift gas 48 is exhausted through port 53, 55, as shown by arrows 56, 58. Product ions 44 of different molecules attain different terminal velocities related to their collision cross section, charge, temperature and pressure, so that the presence of molecules of a constituent gas in a particular sample can be determined by sampling the detector output on lead 59 at predetermined times or spectrum delayed from the initial gating pulse applied to shutter grid 17. When ions 44 reach collector 46, positive or negative charge is collected by collector 46, and carried over lead 60 to an input of electrometer amplifier 61 which amplifies and measures the current received by collector 46. Collector 46 as described here is also a Faraday plate. Electrometer amplifier 61 may, for example, include an operational amplifier 62 having a resistor 63 coupled between its input on lead 60 and its output on lead 59. A second input to amplifier 62 may be coupled to ground.

A commercial electrometer amplifier such as current amplifier model 427 from Keithley Co., Cleve., Ohio., U.S.A. may be used instead of electrometer amplifier 61.

The output of grid pulse generator 13 is coupled over lead 14 to an input of clock 64 which measures the time elapsed since the last trigger pulse and provides a proportional signal on lead 65. When the lapse time on lead 65 is correlated with the appearance of a maximum value in ion current, as sensed by the electrometer amplifier 61, the time for various ions to drift through drift region 18 can be measured. Alternatively, ion mobility spectrum (display including all peaks) can be taken with an oscilloscope or similar equipment. The inverse of the lapse time is a measure of the mobility of ions.

The aperture grid is biased above ground resistor 67. A resistor is coupled between ground and lead 68. Capacitor 69 is also coupled between ground and lead 68. Aperture grid 66 shields collector 46 from the effects of induced charge as the ions 44 travel the length of drift region 18, passing through aperture grid 68 to collector 46 and electric noise of the shutter grid gating pulse.

To increase the collecting efficiency of ions at collector produced in reaction region 16, a repeller 21 is between inlet and radioactive material Ni-63 33 and is isolated from housing 12 by insulator ring 38. A conductive mesh may be positioned perpendicular to the direction of ion 45 at repeller 21 to improve the repelling efficiency of ions. Carrier gas 15 and sample gas 9 pass through reaction region 16, as shown by arrows 45, 59, 60 and exhausted through ports 53–55 as shown by arrows 56–58.

Figure 2A:
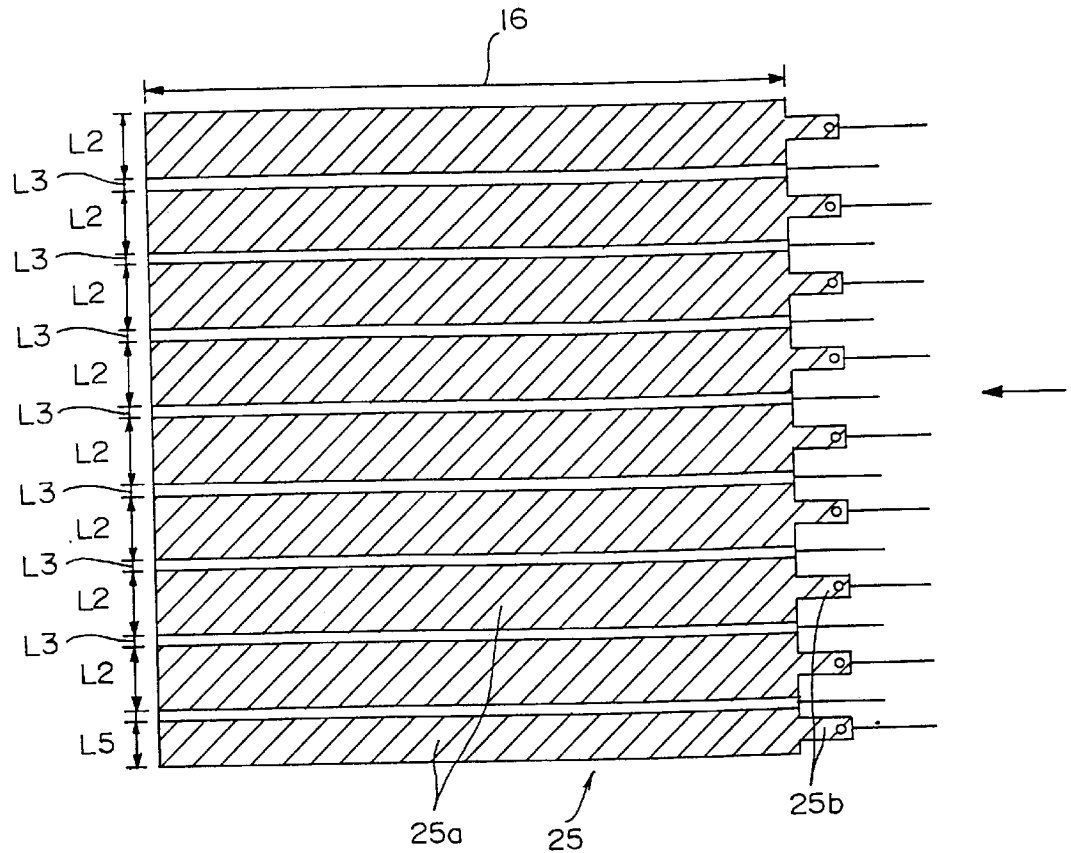
FIGS. 2A and 2B are perspective views each showing flexible printed circuit board of the ion mobility spectrometer of FIG. 1.
Figure 2B:
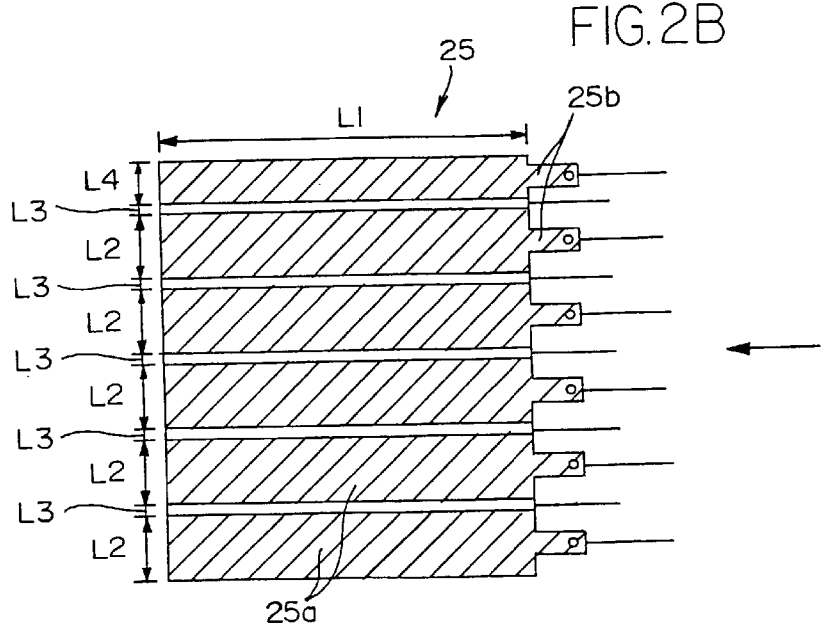

FIG. 2A and 2B are the perspective views of flexible PCBs 34, 35 used in FIG. 1 and the length 11 and 16 of the conductive bands 36, if possible, need to be longer than the circumference of cylinders 22, 23 enclosing reaction regions 16 and drift region 18 respectively. The width 12 and the space 13 of the conductive bands may be changed according to the kind of electric field and structure of reaction region 16 and drift region 18. The uniformity of drift field along the axis of ion movement may be increased when the number of conductive bands increases because the distortion of the drift field along the bands depends inversely on the number of conductive bands. The width of some conductive bands may be changed from 12 to 14 and 15 in FIG. 2A and 2B to maintain a linear electric field near the shutter grid 17.

Just one flexible PCB may be used in the case where the outer diameter of the cylinders surrounding the reaction region and drift region are the same.

What is claimed:

1. An ion mobility spectrometer comprising:

a ion drift tube comprising a reaction region, a shutter grid, a drift region and a collector;

an inlet for introducing a carrier gas into the reaction region;

an ionization source in the reaction region; and at least a first flexible printed circuit board (PCB) having a plurality of bands of conductive material, the PCB fixed onto the surface of the ion drift tube to develop electric fields along the axis of the reaction region and the drift region for the movement of ions generated in the reaction region to the collector.

2. The ion mobility spectrometer according to claim 1, further comprising a second PCB, wherein the first and second PCBs are fixed onto the outer and inner surfaces of the ion drift tube.

3. The ion mobility spectrometer according to claim 1, wherein the first PCB is fixed onto the outer surface of the ion drift tube.

4. The ion mobility spectrometer according to claim 1, wherein the first PCB is fixed onto the inner surface of the ion drift tube.

5. An ion mobility spectrometer comprising:

a ion drift tube having a reaction region, a shutter grid, a drift region and a collector;

an inlet for introducing a carrier gas into the reaction region;

an ionization source in the reaction region; and at least a first and a second flexible printed circuit board (PCB) fixed onto the outer and inner surfaces of the ion drift tube to develop electric fields along the axis of the reaction region and the drift region to cause the movement of ions from the reaction region to the collector.

6. An ion drift tube for use in an ion mobility spectrometer, the drift tube comprising:

a reaction region formed from a dielectric material joined with a printed circuit board (PCB) to form a cylinder, the cylinder having an interior or exterior surface upon which a plurality of bands of conductive material are affixed;

a shutter grid separating said reaction region from a drift region, said drift region formed from a dielectric material joined with a printed circuit board (PCB) to form a second cylinder, said second cylinder having an interior or exterior surface upon which a second plurality of bands of conductive material are affixed;

wherein said first and second plurality of conductive bands are adapted to develop electric fields along an axis of said reaction and drift regions to cause the movement of ions from the reaction region, through said drift region towards a collector.

7. The ion drift tube of claim 6 wherein the dielectric material is coated onto a single printed circuit board to form said first and second cylinders.

8. The ion drift tube of claim 6 wherein said first and second plurality of conductive bands are affixed to the exterior surface of said first and second cylinders, respectively, further including:

a third plurality of conductive bands formed along the interior surface of said first cylinder; and a fourth plurality of conductive bands formed along the interior surface of said second cylinder.

* * * * *